(12) United States Patent
Jahan et al.

(10) Patent No.: US 10,183,000 B1
(45) Date of Patent: *Jan. 22, 2019

(54) 2, 4-DINITROANILINO-BENZOIC ACID: NOVEL INSULINOTROPIC AGENT FOR THE TREATMENT OF DIABETES

(71) Applicants: Humera Jahan, Karachi (PK); Muhammad Iqbal Choudhary, Karachi (PK); Mehwish Manzoor, Karachi (PK); Khalid M. Khan, Karachi (PK); Atta-ur Rahman, Karachi (PK)

(72) Inventors: Humera Jahan, Karachi (PK); Muhammad Iqbal Choudhary, Karachi (PK); Mehwish Manzoor, Karachi (PK); Khalid M. Khan, Karachi (PK); Atta-ur Rahman, Karachi (PK)

( * ) Notice: Subject to any disclaimer, the term of this patent is extended or adjusted under 35 U.S.C. 154(b) by 0 days.

This patent is subject to a terminal disclaimer.

(21) Appl. No.: 15/682,623

(22) Filed: Aug. 22, 2017

(51) Int. Cl.
*A61K 31/192* (2006.01)
*A61K 31/136* (2006.01)
*A61K 31/04* (2006.01)
*A61B 5/145* (2006.01)

(52) U.S. Cl.
CPC ............ *A61K 31/192* (2013.01); *A61K 31/04* (2013.01); *A61K 31/136* (2013.01); *A61B 5/14532* (2013.01)

(58) Field of Classification Search
CPC .... A61K 31/196; C07C 229/64; C07C 229/58
USPC .................................................. 514/166, 567
See application file for complete search history.

(56) References Cited

U.S. PATENT DOCUMENTS

| 9,381,182 | B2* | 7/2016 | Choudhary | .......... A61K 31/196 |
| 9,387,198 | B1* | 7/2016 | Jahan | ................. A61K 31/4184 |
| 2007/0287674 | A1* | 12/2007 | Ahmad | .............. A61K 31/7028 514/26 |
| 2010/0029613 | A1* | 2/2010 | Nedergaard | ......... A61K 31/553 514/212.01 |
| 2015/0051286 | A1* | 2/2015 | Choudhary | .......... A61K 31/196 514/567 |

OTHER PUBLICATIONS (Accession No. 2016:572170; Document No. PREV201600572170, AttaUrRahman [Editor].(2016) pp. 80-102 Frontiers in Medicinal Chemistry, vol. 9. Publisher: Bentham Science Publ, PO Box 294, Busum, 1400, .ISSN: 1567-2042. ISBN: 978-1-68108-250-9(H), 978-1-68108-249-3(P). Document Type: Book; (Book Chapter).*
Jahan et al. IChemico—Biological Interactions 273 (2007) 237-244).*

* cited by examiner

*Primary Examiner* — Sabiha N Qazi
(74) *Attorney, Agent, or Firm* — Sarfaraz K. Niazi

(57) ABSTRACT

The current study established that treatment of diabetes using compound 1(2,4-dinitroanilino-benzoic acid), an anthranilic acid derivative, by restoring the functional activities of the pancreas via its insulinotropic action.

3 Claims, 4 Drawing Sheets

2,4-DINITROANILINO-BENZOIC ACID: NOVEL INSULINOTROPIC AGENT FOR THE TREATMENT OF DIABETES

BACKGROUND OF THE INVENTION

Type 2 diabetes mellitus is a heterogeneous, polygenic disorder of metabolism [Matsuyama A et al. 2009]. The changes in life style pattern and behavior are associated with an increase incidence of type 2 diabetes. The disorder is affecting more than 90% of patients globally [Zimmet P Z et al. 2011, Jahan H et al. 2015].

The pathogenesis of type 2 diabetes involves inadequate secretion of insulin by pancreatic β-cell, and resistance in its action [Cavaghan M K et al. 2000]. The point in the progression of type 2 diabetes when pancreatic β-cells dysfunction emerges is less evident, so far. The proposed mechanisms involved in the dysfunction of beta-cell function include ER stress, glucolipotoxicity, and oxidative stress [Butler A E et al. 2003].

Currently available oral antidiabetic drugs include metformin and sulfonylureas. They play a pivotal role in the treatment of type 2 diabetic patients [Groop L C et al. 1992, Holman R R 2006].

Metformin suppresses glycogen break down and gluconeogenesis in the liver, and hence decreases basal glucose output. It also enhances muscles glucose metabolism in type 2 diabetic patients. However, the most worrisome complication associated with metformin treatment is lactic acidosis [Bodmer M et al. 2008].

Sulfonylureas are insulinotropic in their mechanism of action, and are found effective in majority of diabetic patients. However, few patients are found primary nonresponders to sulfonylureas treatment. In addition, chronic treatment with sulfonylureas may result in secondary failure to treatment [Pontiroli A E et al. 1994]. This may occurs as a result of multiple causes, involving (1) hyperstimulation of insulin producing beta-cells leading to desensitization; (2) persistent insulin secretion associated with the reduction of pancreatic insulin contents; and (3) hyperglycemia-induced beta-cells toxicity. The major concern associated with sulfonylureas treatment is symptomatic hypoglycemia due to sustained insulin release, irrespective of blood glucose levels [Matsuyama A et al. 2009, Pontiroli A E et al. 1994, Hosokawa Y A et al. 1997, Leahy J L 1996, Taverna et al. 2001, Kawaki J et al. 1999]. Moreover, treatment with sulfonylureas may also result in weight gain. It is therefore not the choice for treating obese patients [Bodmer M et al. 2008].

Despite intensive attempts towards long term management of type 2 diabetes, maintaining near euglycemic condition in these patients remains a challenge [Luna B et al. 2001].

Anthranilic acid and its derivatives are constituents of many bioactive molecules with a wide range of biological activities. Indeed, anthranilic acid nucleus serves as a biochemical precursor in the synthesis of amino acid tryptophan and its analogs, and also a major constituent of various alkaloids [Tiwari D et al. 2011, Syed M M et al. 1990]. Both experimental and preclinical studies demonstrated their medicinal properties, including matrix metalloproteinase inhibition, anticancer, anti-inflammatory, and analgesic activities (Syed M M et al. 1990, Cocco M T et al. 2004]. Therefore, the molecules based on anthranilic acid scaffold have gained much attention in drug discovery and development [Suleiman, M M et al. 2014, Thongtan J et al. 2006, DeLuca S et al. 2006].

Our most recent study identified the potential of 2,4-dinitroanilino-benzoic acid, an anthranilic acid derivative, as a novel antiglycating agent of the multiple stages of non-enzymatic glycation process (FIG. 1) [Choudhary M I. U.S. Pat. No. US9381182B2].

Keeping in view of the medicinal significance of anthranilic acid, the current study discovered the potential of anthranilic acid derivative, 2,4-dinotroanilino-benzoic acid (1), as an insulinotropic agent in the treatment of diabetes.

BRIEF SUMMARY OF THE INVENTION

The pancreatic beta-cell failure played a critical role in the pathogenesis of diabetes. Type 2 diabetic patients have defects in both beta-cells mass and function. The current failure to oral antidiabetic agents demands urgent identification of novel hypoglycemic agents with superior efficacy. The current invention evaluated the potential of novel compound 1, an anthranilic acid derivative, for insulinotropic action in streptozotocin (STZ)-mediated pancreatic beta-cell lesions in diabetic rats. Dining an eight week of intervention study, fasting blood glucose levels, serum insulin levels, and pancreatic insulin contents were measured in three different groups of Wistar rats; control, STZ-induced diabetic, and anthranilic acid derivative-treated diabetic rats. Beta-cell number and islet area were also quantified, and immuno-histochemical study was performed. We discovered that Compound 1 showed antidiabetic effects by improving glucose levels, serum insulin levels, and plasma insulin contents in the treated group. Compound 1 exhibited a significant insulinotropic action on STZ-induced diabetic pancreas, and caused an increased immunoreactivity for insulin, as compared to STZ-induced diabetic group.

DETAILED DESCRIPTION OF THE INVENTION

Figure 1:
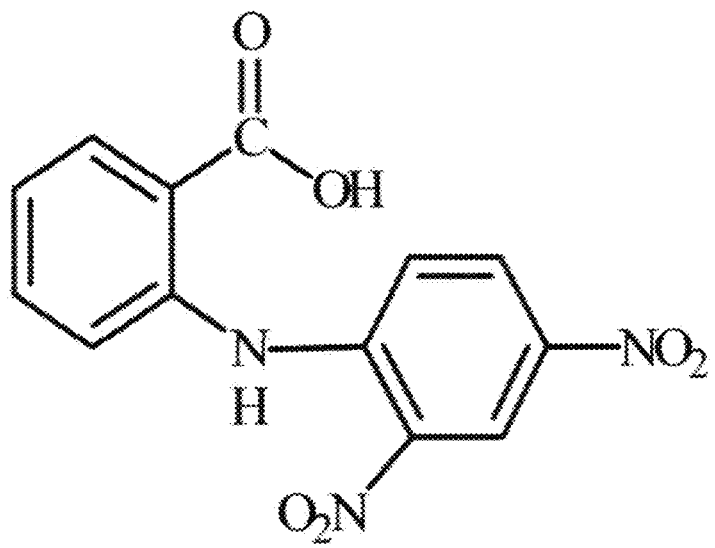
FIG. 1 depicts compound 1(2,4-Dinitroanilino-benzoic acid), a novel insulinotropic agent.

The current invention relates to the discovery of novel agent that may have insulinotropic effect on pancreatic beta-cells.

EXAMPLE 1

Animals and Induction of Diabetes

Animals: Eight weeks old Wistar rats (n=54; 24 males: 30 females) weighing 160-180 g were used in the study. During the eight weeks of the experiment, animals were kept in the animal house with a controlled temperature (25±2°C.), and 12 hours light/dark cycle. Water and standardized food access were provided at libitum.

Diabetes Induction: Prior to induction of diabetes, animals were given a high-fat diet (40% fat content) for two weeks. Diabetes was induced by administrating intraperitoneally a single dose of freshly prepared solution of streptozotocin (45 mg/kg) (Wako, Richmond, USA) in a chilled 0.1 M citrate buffer, pH 4.5. The normal control rats were injected with citrate buffer alone. Fasting blood glucose levels (FBG) were measured after 48 hours, and one week of diabetes induction with a blood glucose analyzer (Accu-Chek®, Roche, Mannheim, Germany). Rats with FBG levels of ≥200 mg/dL were considered diabetic, and randomly divided into diabetic and a compound 1-treated (100 mg/kg) groups. Initially the therapeutic dose of compound 1 was optimized in STZ-induced diabetic rats, using various concentrations; such as 25, 50, and 100 mg/kg, and the dose dependent anti-diabetic effect was observed with a significant effect at 100 mg/kg of body weight. Moreover, daily oral administration of compound 1 for eight weeks was without significant mortality. This indicated the safety of doses up to 100 mg/kg of body weight.

EXAMPLE 2

Biochemical Parameters

Blood glucose levels and body weight of each group were monitored on weekly basis under fasting states. Blood samples were drawn from tail vein to measure the glucose levels by blood glucose analyzer. After 8 weeks of the experiments, rats under 8 hours of fasting states were anaesthetized by phenobarbital sodium (60 mg/kg), and blood samples were collected via cardiopuncture. Serum was stored at −80° C. until measurement of the insulin levels. A part of cryopreserved isolated pancreas was used for the measurement of pancreatic insulin contents. Briefly, pancreas were homogenized in an acid-ethanol solution (75% ethanol, 1.5% HCl, and 23.5% deionized water), and the mixture was kept for 4 hours at 4° C. to extract the insulin. Serum- and isolated pancreatic insulin contents were measured by rat insulin ELISA kit (Amersham Biosciences, N.J., USA).

Figure 2:
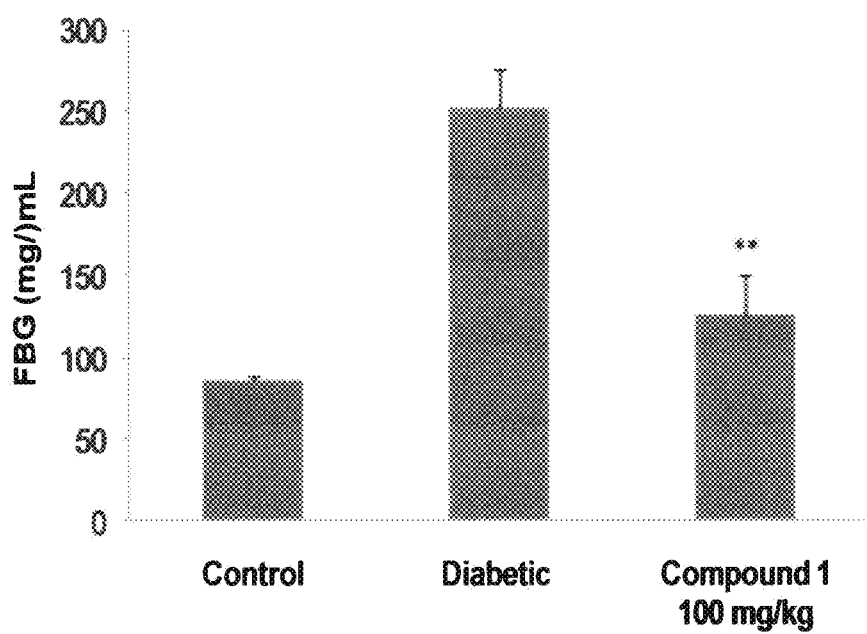
FIG. 2 depicts the effect of compound 1 on FBG (mg/dL) in STZ-induced diabetic rats. The changes in blood glucose level after eight weeks of treatment. The values represented from each group (n=6) as mean ±SEM. **P<0.01 vs diabetic group.

Results: During eight weeks of intervention study, no gain in body mass was observed in compound 1-treated (100 mg/kg) group (Table 1). STZ-induced diabetic rats had a lower body mass than the normal control rats as a consequence of marked deficiency of insulin. Long term treatment of compound 1 (100 mg/kg of body weight) improved the blood glucose levels, with a significant reduction in FBG levels (FIG. 2) (Table 1), as compared to untreated diabetic group. These results indicated a masked alteration in pancreatic insulin contents and serum insulin levels. These parameters were, therefore, investigated in all groups.

Figure 3:
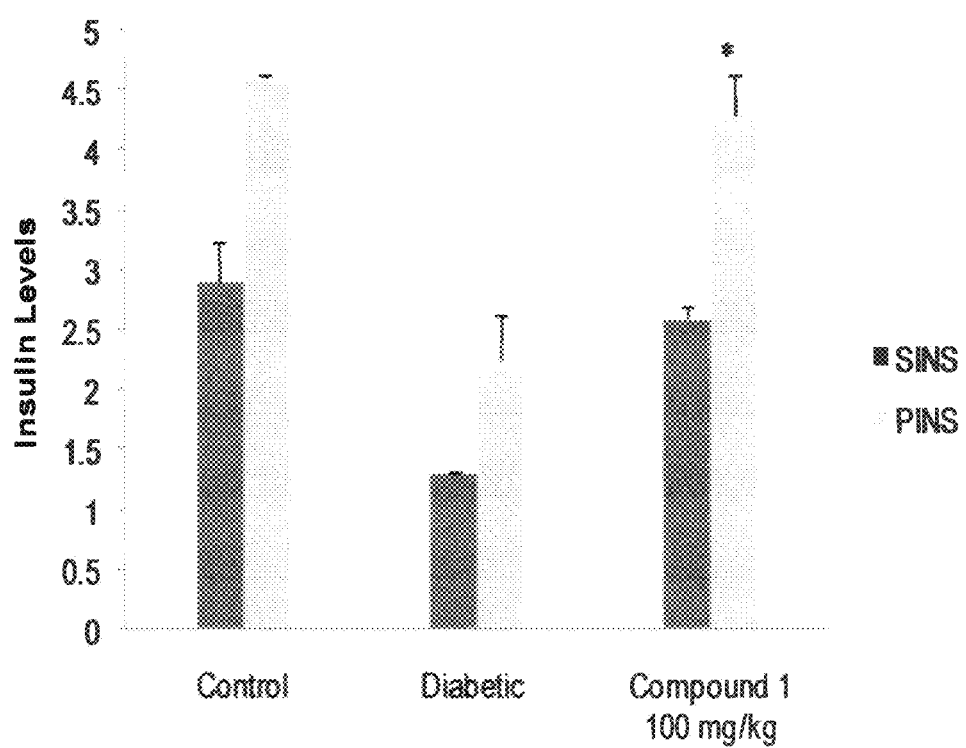
FIG. 3 illustrates serum and pancreatic insulin levels. Pancreatic insulin content (ng/mg of pancreas) and serum insulin levels (ng/mL) were measured after 8 weeks of treatment with compound 1 (100 mg/kg) in STZ-induced diabetic rats. The values represented from each group (n=6) as mean ±SEM. *P<0.05 vs diabetic group.

In comparison with STZ-induced diabetic group, compound 1-treated (100 mg/kg) group revealed a marked increase in serum insulin levels, as observed in untreated control group. Improvement in serum insulin levels in compound 1-treated (100 mg/kg) group was found to be increase in pancreatic insulin contents (p<0.05) (FIG. 3), as measured by acid-ethanol extraction method.

EXAMPLE 3

Islets Histopathology and Immunohistochemistry

Procedure: Pancreata isolated from rats were fixed with 3.7% neutral buffered formalin and embedded in paraffin. The 5 μm thick sections (n=6/group) were stained with eosin and hematoxilin, and evaluated for islets histopathology, after performing deparaffinization and dehydration steps. For immunohistochemistry analysis, briefly the antigen was first retrieved by heating for 40 min at 90° C. in 5.0 mM citrate buffer, pH 4.5. Prior to primary antibody treatment, each section was then cooled at room temperature, and incubated with 1× rotti immunoblocking solution (Carl Roth, Karlsruhe, Germany). The sections were immunostained with mouse K36AC10 monoclonal anti-insulin antibody (1:2,000) (Sigma Aldrich, St. Louis, Mo., USA) for 1 hour in a dark humidified chamber at 37° C. The sections were then immunostained with Alexa Fluor 594 donkey anti-mouse IgM secondary antibody (1:200)(Jackson ImmunoResearch, Pa., USA) for 1 hour in a dark chamber at 37° C. for detention. Finally, beta cells nuclei were stained with DAPI (1:5,000) (Sigma Aldrich, St, Louis, Mo., USA). The stained sections were observed under Nikon 90i microscope, equipped with DXM-1200 digital camera (Nikon, Tokyo, Japan).

Figure 4A:
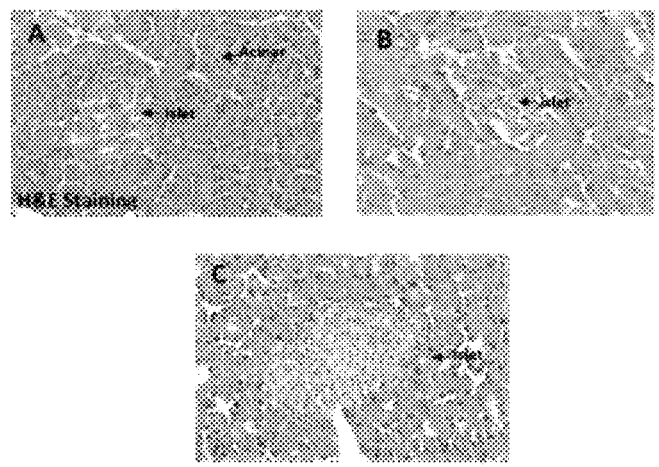
FIG. 4A illustrates histopathological findings of pancreatic islet in diabetic Wistar rats, using hematoxilin and eosin (H&E) staining. (A) Normal rat pancreas showing beta cell are spread throughout the islet, (B) Diabetic pancreatic section with marked islet atrophy; but no sign of inflammatory infiltration was observed, and (C) Compound 1 (100 mg/kg)-treatment markedly attenuated the STZ-induced islet atrophy in diabetic rats. Magnification 200×.
Figure 4B:
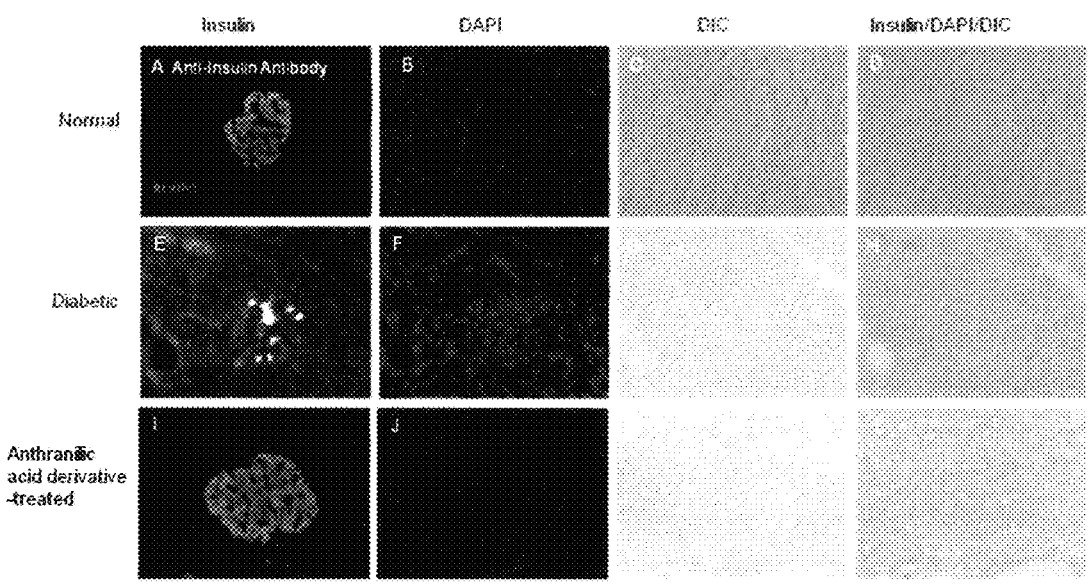
FIG. 4B illustrates representative pancreatic islet sections showing immunofluorescent staining for insulin. (A) Normal Wistar rat pancreatic section showing immunopositive beta cell (A-D), (B) Diabetic untreated with marked decrease in immunopositive beta-cell following STZ-induced type 2 diabetes (E-H), and (C) Compound 1 (100 mg/kg) restored the residual beta-cell function after STZ-induced beta cells destruction (I-L). The insulin (red), nucleus (blue), and DIC image, triple merged. Magnification 200×.

Results: Histopathological assessment of pancreata of diabetic rats exhibited a frequency of degenerative changes, such as a marked decreased in immunopositive beta-cell, islet degeneration, and atrophy, but no sign of inflammatory cells infiltration were observed (FIG. 4A and 4B). In contrast, degenerative changes due to STZ injection and hyperglycemic environment were significantly attenuated with compound 1(100 mg/kg) treatment.

EXAMPLE 4

Quantification of Pancreatic Islet Area and Beta-Cell Number

Procedure: The pancreatic islet area ($\mu_2$) and the beta-cell number were quantified from overlapped images of pancreas that was immunostained with insulin and DAPI in all islet sections using NIS-Elements image analysis software AR 3.0. The pancreatic islet area ($\mu_2$) and the beta-cell number per section were enumerated by using five sections per pancreas, and five rats from each group.

Figure 5A:
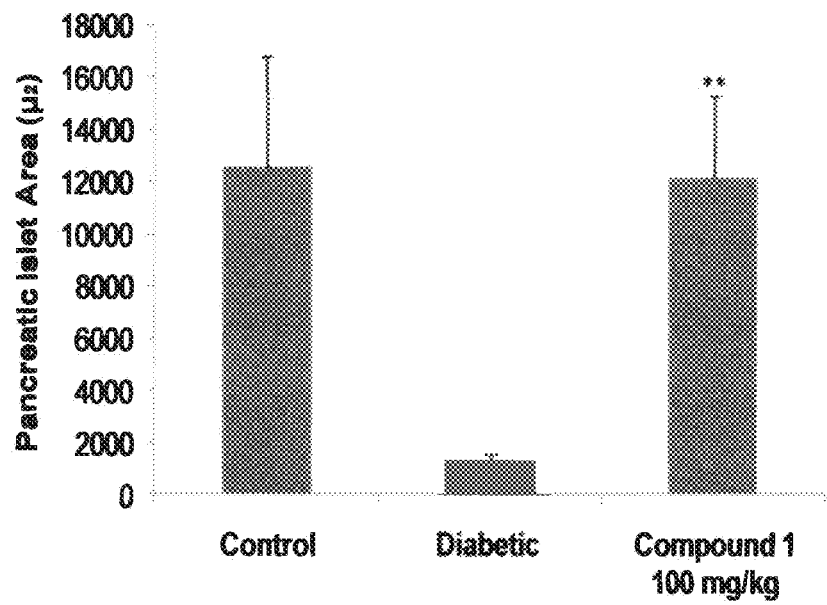
FIG. 5A illustrates pancreatic islet area and beta-cell number and pancreatic islet area ($\mu_2$) were measured per pancreas section (n=5) from each group.
Figure 5B:
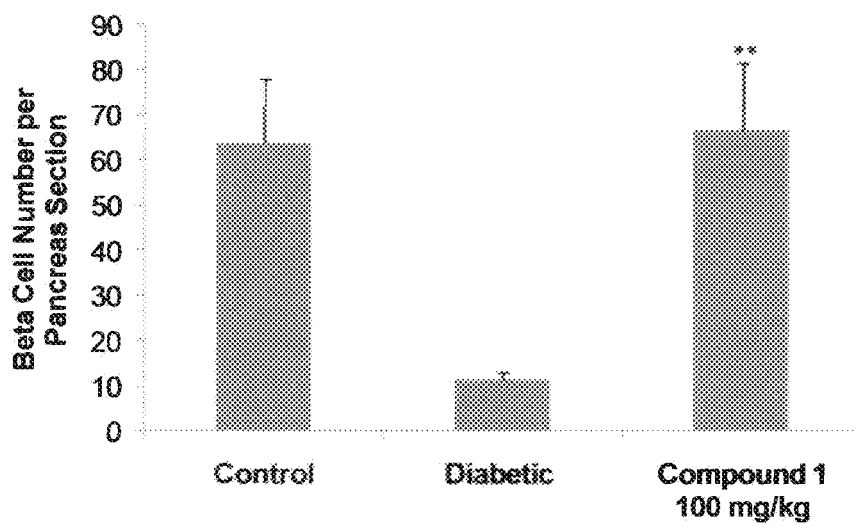
FIG. 5B depicts pancreatic beta cell number estimated per pancreas section (n=5) from each group. The values represented from each group (n=5) as mean ±SEM. **P<0.05 vs diabetic group.

Results: The physiological relevance of the above presented results with the islet beta-cell number and islet area was determined. The STZ injection (45 mg/kg) in diabetic Wistar rats showed a marked deterioration of pancreatic beta-cells with accompanying reduction in islet area and pancreatic insulin contents, as calculated by merged immunostained images (FIG. 5A and 5B). While, the treatment with compound 1 (100 mg/kg) significantly restored the beta-cell number, the islet area, and the insulin contents.

EXAMPLE 5

Statistical Analysis: All results are expressed as means ±SEM. The significance of differences between groups was determined by using one-way ANOVA, and multiple comparisons were performed by Tukey Alpha, post hoc analysis. The entire statistical analyses were carried out by using IBM SPSS 16.0 software. Differences of P<0.05 were considered significant

TABLE 1

Antidiabetic effect of anthranilic acid derivative (1) in diabetic rat.

|  | Control | Diabetic | Anthranilic acid derivative (1) |
|---|---|---|---|
| FBG (mg/dL) | 87 ± 2.2 | 252 ± 10 | 126 ± 8* |
| Body weight (g) | 176 ± 1.9 | 152 ± 5.9 | 160 ± 2.1* |

The values represent the mean ± SE for 06 rats in each group
*P <0.05 vs diabetic group

What is claimed is:

1. A method of treatment of diabetes comprising administering to humans or animals in need, an effective amount of 2,4-dinitroanilino-benzoic acid, in a dosage form further comprising inert ingredients.

2. The method of claim 1, wherein administration of 2,4-dinitroanilino-benzoic acid reduces glucotoxity on islet-beta cell by restoring beta cell numbers in pancreas.

3. The method of claim 1, wherein the effective amount is 100 mg/kg body weight.

* * * * *